United States Patent [19]
Greep

[11] Patent Number: 6,039,735
[45] Date of Patent: Mar. 21, 2000

[54] ELECTRIC FIELD CONCENTRATED ELECTROSURGICAL ELECTRODE

[75] Inventor: Darcy W. Greep, South Jordan, Utah

[73] Assignee: MegaDyne Medical Products, Inc., Draper, Utah

[21] Appl. No.: 08/943,551

[22] Filed: Oct. 3, 1997

[51] Int. Cl.[7] .................................................. A61B 17/39
[52] U.S. Cl. ............................................... 606/45; 606/49
[58] Field of Search ................................ 606/41, 45, 49

[56] References Cited

U.S. PATENT DOCUMENTS

| | | |
|---|---|---|
| 4,534,347 | 8/1985 | Taylor . |
| 4,674,498 | 6/1987 | Stasz . |
| 4,785,807 | 11/1988 | Blanch . |
| 5,380,320 | 1/1995 | Morris ........................................ 606/45 |
| 5,643,256 | 7/1997 | Urueta ........................................ 606/45 |
| 5,693,050 | 12/1997 | Speiser ...................................... 606/45 |
| 5,697,926 | 12/1997 | Weaver ...................................... 606/45 |
| 5,702,387 | 12/1997 | Arts et al. ................................. 606/45 |

*Primary Examiner*—Lee Cohen
*Attorney, Agent, or Firm*—Workman, Nydegger & Seeley

[57] ABSTRACT

An electric field concentrated electrosurgical electrode (e.g., blade or the like) wherein there is provided a conducting member having an edge that is at least partly sharpened and coated with electrical insulating material so as to produce a highly concentrated electric field and a highly concentrated transfer of electric energy thereacross by capacitive coupling. In the preferred embodiment, the working surfaces of a sharpened surgical implement, including the sharpened part, are entirely coated with a layer of non-stick insulating material.

18 Claims, 2 Drawing Sheets

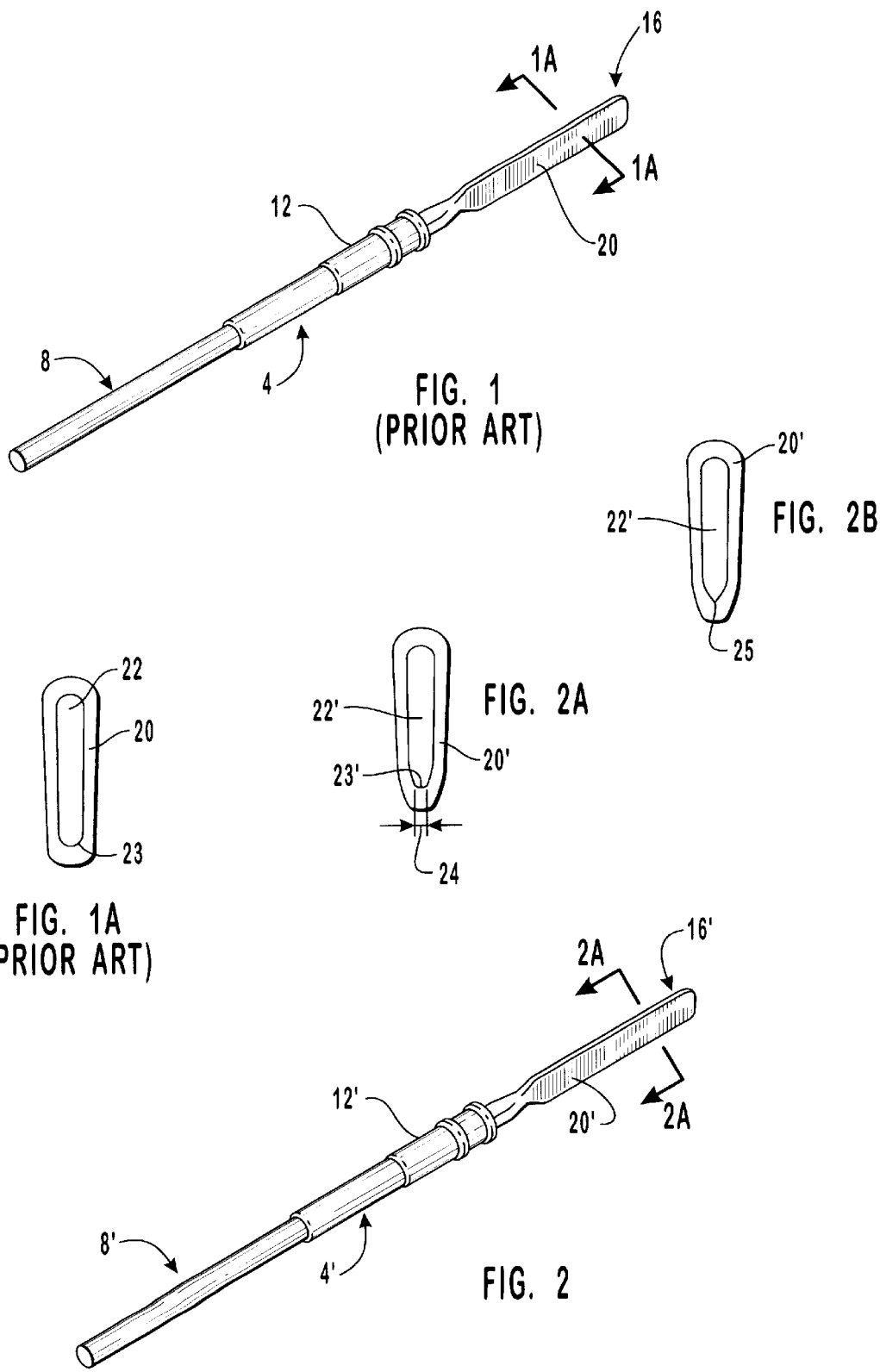

ELECTRIC FIELD CONCENTRATED ELECTROSURGICAL ELECTRODE

BACKGROUND OF THE INVENTION

This invention relates to electrosurgery and more particularly to electrosurgical electrodes (e.g., probes or blades) for use in performing electrosurgery.

As is known to those skilled in the art, modem surgical techniques typically employ radio frequency (RF) cautery to cut tissue and coagulate the same to stop bleeding encountered in performing surgical procedures. For historical perspective and details of such techniques, reference is made to U.S. Pat. No. 4,936,842.

As is known to those skilled in the medical arts, electrosurgery is widely used and offers many advantages including that of the use of a single surgical tool for both cutting and coagulation. A variety of proposals have heretofore been embodied in existing electrosurgical implements. Examples of such proposals include those set forth in U.S. Pat. No. 4,534,347 granted to Leonard S. Taylor Aug. 13, 1985, U.S. Pat. No. 4,674,498 granted to Peter Stasz Jun. 23, 1987, and U.S. Pat. No. 4,785,807 granted to G. Marsden Blanch on Nov. 22, 1988.

The first two of the foregoing patents illustrate implements having sharpened exposed edges (e.g., knife-blade like geometries) which are employed to perform conventional mechanical cutting of tissue. The last of the patents sets forth an unsharpened blade which has been entirely coated with an insulating layer so that cutting is performed by electrical energy capacitively transferred across the insulating layer rather than by conventional mechanical action. Thus, in electrosurgery, "cutting" is accomplished when energy transfer is sufficient to cause water in tissue cells to boil, thus rupturing the cell membranes by internal rather than external forces. High energy is required to effect such electrosurgical cutting. While the Blanch proposals have constituted an important advance in the art and have found wide-spread acceptance in the field of electrosurgery, there has been a continuing need for further improvement in electrosurgery to reduce thermal necrosis thereby decreasing post-operative complication, to reduce eschar production, to reduce incidence of heat damage to tissue away from the cutting site, and to increase the speed of cutting.

BRIEF SUMMARY OF THE INVENTION

The present invention provides a marked improvement in performance over the proposals heretofore made by achieving an important concentration of electrosurgical energy to permit more rapid and effective cutting at lower RF energy levels. This is accomplished by shaping the geometrical surface(s) to be used to effect electrosurgical cutting to concentrate energy transfer. Such surfaces are an edge or point of the electrically conducting interior part of the implement which, after being completely coated with insulation, no longer presents a particularly sharp exterior geometrical surface for mechanical contact with patient tissue but which, because of a concentration of electric field and energy transfer (as hereinafter described) provides a marked improvement in charge concentration and tissue severance to permit utilization of lower energy levels and results in reduced thermal necrosis, more rapid cutting, and reduced eschar production. The principles hereof may not only be applicable to blades and points, but also to modified ball electrodes, L-hooks, L-wires, J-hooks and similar constructions.

OBJECTS AND FEATURES OF THE INVENTION

It is one general object of the invention to improve electrosurgical implements.

It is another object of the invention to focus and/or concentrate electrosurgical energy in electrosurgical implements.

It is yet another object of the invention to improve accomplishment of surgical procedures through electrical, as contrasted with mechanical, cutting of tissue.

Accordingly, in accordance with a feature of the invention, an electrosurgical implement is structured geometrically to include one or more working regions at which electric fields are focused, thus concentrating such fields to improve surgery.

In accordance with yet another feature of the invention, the aforementioned concentration of electric fields results in a corresponding increase in focused transfer of electrical energy to defined locations and thus lessens undesired transfer to adjacent tissue.

In accordance with still another feature of the invention, the aforementioned concentration of energy permits use of reduced levels of electrosurgical power thus further facilitating use.

These and other objects and features of the invention will be apparent from the following description, by way of example of preferred embodiments, with reference to the drawing.

BRIEF DESCRIPTION OF THE DRAWING

FIG. 1 is a perspective view illustrating an implement representative of the prior art;

FIG. 1A is a sectional view taken along section lines 1A—1A of FIG. 1;

FIG. 2 is a similar perspective view of an implement embodying principles according to the invention;

FIG. 2A is a sectional view taken along the section lines 2A—2A of FIG. 2 and depicting a partly sharpened working surface;

FIG. 2B is a drawing similar to that of FIG. 2A except for the working surface of the implement which is depicted as a knife edge;

DESCRIPTION OF A PREFERRED EMBODIMENT

Figure 3:
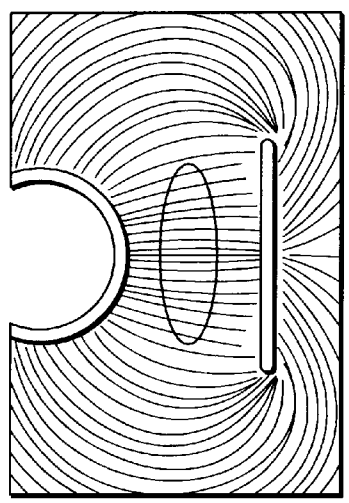
FIG. 3 is a view illustrating a typical electric field existing between a rounded surface implement and a working return electrode.

Now turning to the drawing, and more particularly FIG. 1 and 1A thereof, it will be seen to depict an implement representative of the prior art as set forth in the aforementioned Blanch U.S. Pat. No. 4,785,807. There, are seen an electrosurgical knife, generally shown at 4, having a proximal end 8 fitted with a sleeve fitting 12 positioned around the knife shank to provide protection and to facilitate holding of the knife by a conventional holder (not shown). The knife also includes a distal end 16 formed with unsharpened cutting surface 23 as shown. A coating 20 of non-stick material covers the surface area 22 of the electrode blade and serves to eliminate or reduce the clinging of charred tissue to the blade.

FIG. 2 depicts an implement which embodies the principles underlying the instant invention. There, in FIG. 2 is seen an instrument appearing similar to that of FIG. 1. Thus, in FIG. 2 there is seen an electrosurgical knife, generally shown at 4', having a proximal end 8' fitted with a sleeve fitting 12' positioned around the knife shank to provide protection and to facilitate holding of the knife by a conventional electrosurgical holder (not shown). The knife also includes a distal end 16' which is formed with a special geometrical shape as described in connection with FIGS. 2A, 4 and 5. A coating 20 of non-stick material covers the surface area of the cutting blade and serves to eliminate or reduce the clinging of charred tissue to the blade. In sharp contrast with the embodiment of FIG. 1, however, the embodiment of the instant invention illustrated in FIG. 2 features a cross sectional geometry which includes an edge that is at least partly sharpened as shown in FIG. 2A.

As mentioned above, FIG. 2A is a sectional view taken along the section lines 2A—2A of FIG. 2. There, it will be seen are electrically conductive main body 22 which may be of any suitable material such as, preferably, surgical grade stainless steel. Body 22 has been at least partly sharpened at its lower extremity to an edge 23' which, as described in connection with FIGS. 3 and 4 concentrates or focuses the electric field created when electrical potential is applied to the blade, thus increasing the concentration of transferred electrical energy and correspondingly improving efficiency with which the implement achieves a cutting action, e.g., severs tissue. Before leaving FIG. 2A, it should be understood that while the preferred geometry embodies a fully sharpened edge (or point) such as that depicted in FIG. 2B, the efficacious characteristics flowing from the invention begin to be significantly observed when the dimension 24 (i.e., working edge width) is at or less than 0.2 mm, thus presenting a working edge width of 0.2 mm or less; and such efficacious characteristics further improve as the dimension 24 is reduced to a knife edge.

Now turning to FIG. 2B, there will be seen a configuration similar to that of FIG. 2A except that in FIG. 2B there is depicted a fully sharpened blade having a knife edge 25.

Figure 4:
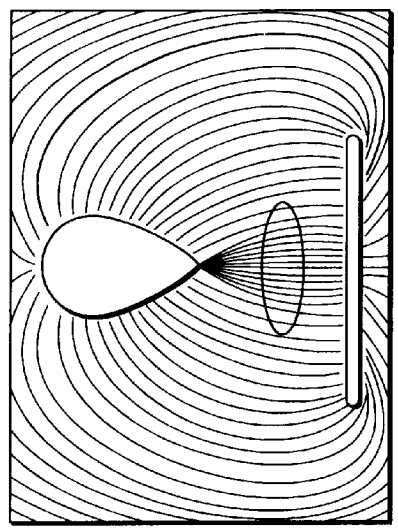
FIG. 4 is a view illustrating modified electric field concentration associated with a sharply pointed geometry.

The physical principles underlying the foregoing marked improvement can be understood from reference to FIGS. 3 and 4. FIG. 3 is a diagram illustrating electric field pattern lines for an electric field existing between a conductor or electrode 30 having an annular, or curved, exterior surface 31 and a counter electrode 32. Although electrode 30 is shown as being hollow, the electric field pattern shown will be essentially the same if the electrode were solid. It will now be seen that the density of the electric field lines within ellipse 33 is nearly uniform and thus the electric field does not vary substantially within that region. However, in FIG. 4, it will be noted that if the geometry of electrode 40 is made to include a pointed region as represented by point or edge 41, the corresponding electric field becomes much more concentrated as represented by the much greater line density of electric field lines (within the ellipse 43) between the electrode 40 and counter electrode 42. Thus, on an irregularly shaped conductor, charge tends to accumulate at locations where the curvature of the surface is greatest, that is, at sharp points or edges. By sharpening the blade edge in accordance with the invention hereof, the charge is concentrated along a much smaller surface area or region thus focusing the electric field lines into a tighter arrangement which reduces extraneous charge loss in tissue which is not in close proximity to the point or sharpened edge. The cutting edge of the electrode need not be sharply pointed, it need only be shaped (sharpened) to concentrate energy transfer to the degree desired for optimum cutting.

By way of illustration, the conventional electrode of FIG. 1 has an edge 23 thickness of about 0.33 mm and in the cutting mode may utilize a power setting nearing 40 watts. When sharpened to an edge 23' thickness of about 0.00735 mm, a "sharpness" below that required of a mechanical scalpel blade, the electrode of FIG. 2 can quickly cut through tissue at less than 20 watts, a power setting of 50% less than that required for the electrode of FIG. 1. Moreover, such blade of FIG. 2 cuts more rapidly with less resistance, less eschar production, less thermal necrosis, and improved operator control.

Figure 5:
FIG. 5 is a simplified view illustrating a typical concentration of electric field projected from the partly sharpened edge of FIG. 2A.

The foregoing principles are illustrated in FIG. 5. As noted above, FIG. 5 is a simplified view illustrating a typical concentration of electric field projected from the sharpened edge of FIG. 2A. To facilitate clarity and simplicity of presentation, only lines 53 representing the electric field in the direction of the sharpened point or edge 23' are shown.

It will be observed that the electrode of FIG. 5 is that earlier illustrated in FIG. 2A. Thus, there are shown electrically conductive main body 22 with at least partly sharpened edge or point 23' completely coated with insulating coating 20'. When electrosurgical potential is applied to body 22 in the presence of tissue for which severance is desired, the density of energy transfer is concentrated at the apex 23' as represented by the longer rays within bundle of rays 53. Thus, in the illustrated example, energy is concentrated along the principal axis of main body extended from edge 23'.

The insulating coating 20' may be any of the known several non-stick materials that have been found attractive for use in electrosurgery and applied by any of the known techniques. Thus, in accordance with the preferred embodiment hereof, such material is a fluorinated hydrocarbon (PTFE), an example of which is that which is commercially available under the trade name Teflon. However, other coatings such as a thin layer of diamond material or other known insulator suitable for use in contact with human tissue may be alternatively employed.

The thickness of the non-stick material is that sufficient to ensure transmission of radio-frequency electrical energy from the coated main body to the tissue of the patient essentially exclusively by capacitive coupling, ordinarily less than 1 mil. The precise optimum thickness will vary depending upon the material used and can be readily determined by routine experimentation. It will be evident that this coating "dulls" any sharp electrode edge, but as previously noted, cutting by electrosurgery does not utilize or require sharp surgical edges for mechanically severing tissue. Rather, the cutting is effected by utilizing sufficient energy to cause water in the tissue cells to boil and rupture the cell membranes.

It will now be evident that there has been described herein an improved electrosurgical implement which provides a marked improvement in performance.

Although the invention hereof has been described by way of a preferred embodiment, it will be evident that adaptations and modifications may be employed without departing from the spirit and scope thereof.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. An electrosurgical electrode member comprising a conducting electrode having a main body adapted for communicating radio frequency electrical energy to patient tissue for performing operative procedures thereupon, an insulating coating covering said main body, and energy concentration means including a working edge having an edge thickness of about 0.2 mm or less for concentrating electrical energy transferred across said insulating coating from said body to said patient tissue.

2. A member according to claim 1 wherein said insulating coating entirely covers said working edge.

3. A member according to claim 1 wherein a part of said working edge is partly sharpened.

4. A member according to claim 1 wherein said concentrating means includes said insulating coating and wherein said insulating coating is a chlorinated hydrocarbon.

5. A member according to claim 4 wherein said working edge is formed from a single unitary edge only.

6. A member according to claim 1 wherein said insulating coating comprises non-stick material.

7. A member according to claim 1 wherein said insulating coating comprises a fluorinated hydrocarbon material or diamond.

8. A member according to claim 7 wherein said insulating coating consists essentially of diamond.

9. A member according to claim 7 wherein said insulating coating consists essentially of a fluorinated hydrocarbon material.

10. An electrosurgical member comprising a conducting electrode having a main body adapted for communicating radio frequency electrical energy to patient tissue for performing operative procedures thereupon, an insulating coating covering said main body, and energy concentration means including a working edge having a thickness of about 0.2 mm or less for concentrating electrical energy transferred across said insulating coating from said main body to said patient tissue essentially exclusively by capacitive coupling.

11. A member according to claim 10 wherein said insulating coating entirely covers said working edge.

12. A member according to claim 10 wherein said insulating coating comprises a non-stick material.

13. A member according to claim 10 wherein said insulating coating comprises fluorinated hydrocarbon material.

14. A member according to claim 10 wherein said insulating coating comprises a non-stick material or diamond.

15. A member according to claim 14 wherein said insulating coating consists essentially of diamond.

16. A member according to claim 14 wherein said insulating coating consists essentially of said non-stick material.

17. An electrosurgical electrode member comprising:

a conducting electrode member provided with a main body being adapted for communicating radio frequency electrical energy to a patient's tissue for performing operative procedures thereupon, said main body having a working edge with an edge width of about 0.2 mm or less and being configured to concentrate the radio frequency electrical energy used to perform operative procedures;

and an insulating coating covering said main body, said insulating coating provided with a thickness sufficient to ensure transmission of radio-frequency electrical energy from said main body to said tissue essentially exclusively by capacitive coupling.

18. A member according to claim 17 wherein said working edge is in the form of a sharply pointed projection.

* * * * *

UNITED STATES PATENT AND TRADEMARK OFFICE
CERTIFICATE OF CORRECTION

PATENT NO. : 6,039,735
DATED : March 21, 2000
INVENTOR(S) : Darcy W. Greep

It is certified that error appears in the above-identified patent and that said Letters Patent are hereby corrected as shown below:

Col. 1, ln. 8: after "art," and before "surgical" change "modem" to --modern--

Signed and Sealed this

Tenth Day of April, 2001

Attest:

NICHOLAS P. GODICI

Attesting Officer     *Acting Director of the United States Patent and Trademark Office*